(12) United States Patent
Shah et al.

(10) Patent No.: US 7,355,698 B2
(45) Date of Patent: Apr. 8, 2008

(54) HIGH THROUGHPUT IMAGING DEVICE AND METHOD

(75) Inventors: Shishir Shah, Houston, TX (US); Glenn F. Spaulding, Houston, TX (US)

(73) Assignee: Spin Diagnostics, Inc., Houston, TX (US)

( * ) Notice: Subject to any disclaimer, the term of this patent is extended or adjusted under 35 U.S.C. 154(b) by 0 days.

(21) Appl. No.: 11/379,845

(22) Filed: Apr. 24, 2006

(65) Prior Publication Data

US 2006/0238765 A1  Oct. 26, 2006

Related U.S. Application Data

(60) Provisional application No. 60/674,520, filed on Apr. 25, 2005.

(51) Int. Cl.
*G01N 21/03* (2006.01)
(52) U.S. Cl. ..................................................... 356/246
(58) Field of Classification Search ...................... None
See application file for complete search history.

(56) References Cited

U.S. PATENT DOCUMENTS

| | | | |
|---|---|---|---|
| 4,778,763 A * | 10/1988 | Makiguchi et al. | ........... 436/47 |
| 5,122,284 A | 6/1992 | Braynin et al. | |
| 5,126,544 A | 6/1992 | Izumi | |
| 5,324,629 A | 6/1994 | Phi-Wilson et al. | |
| 5,352,879 A | 10/1994 | Milch | |
| 5,439,645 A | 8/1995 | Saralegui et al. | |
| 5,582,795 A | 12/1996 | Nishina et al. | |
| 5,639,428 A | 6/1997 | Cottingham | |
| 5,814,279 A | 9/1998 | Biesel et al. | |
| 6,111,636 A * | 8/2000 | Tuunanen | ................... 356/213 |
| 6,127,187 A | 10/2000 | Clampitt | |
| 6,135,940 A | 10/2000 | Walters | |
| 6,254,834 B1 | 7/2001 | Anderson et al. | |
| 6,893,877 B2 | 5/2005 | Hunter et al. | |
| 2002/0149736 A1 | 10/2002 | Tsukada | |

FOREIGN PATENT DOCUMENTS

| | | |
|---|---|---|
| DE | 2154066 | 5/1972 |
| JP | 63289441 | 11/1988 |

* cited by examiner

*Primary Examiner*—Tu T Nguyen

(57) ABSTRACT

An imaging device and system for the high throughput imaging of multi-sample containers is described. Generally speaking, one or more containers capable of holding multiple sample volumes are fixed to a platform which is rotated during image acquisition operations. Images of sample volumes are obtained by moving an imaging device (e.g., a camera) from a first position to a second position across the one or more sample volumes. Because the platform is continuously rotated there is no lost time due to moving the samples (e.g., acceleration, deceleration and backlash compensation). Movement artifacts associated with motion of the imaging device occur in those times when the imaging device is "between" sample volumes, thereby eliminating any lost time due to this motion. Rather than, or in combination with, the aforementioned lights sources, additional light sources may be added to provide epi-illumination.

33 Claims, 5 Drawing Sheets

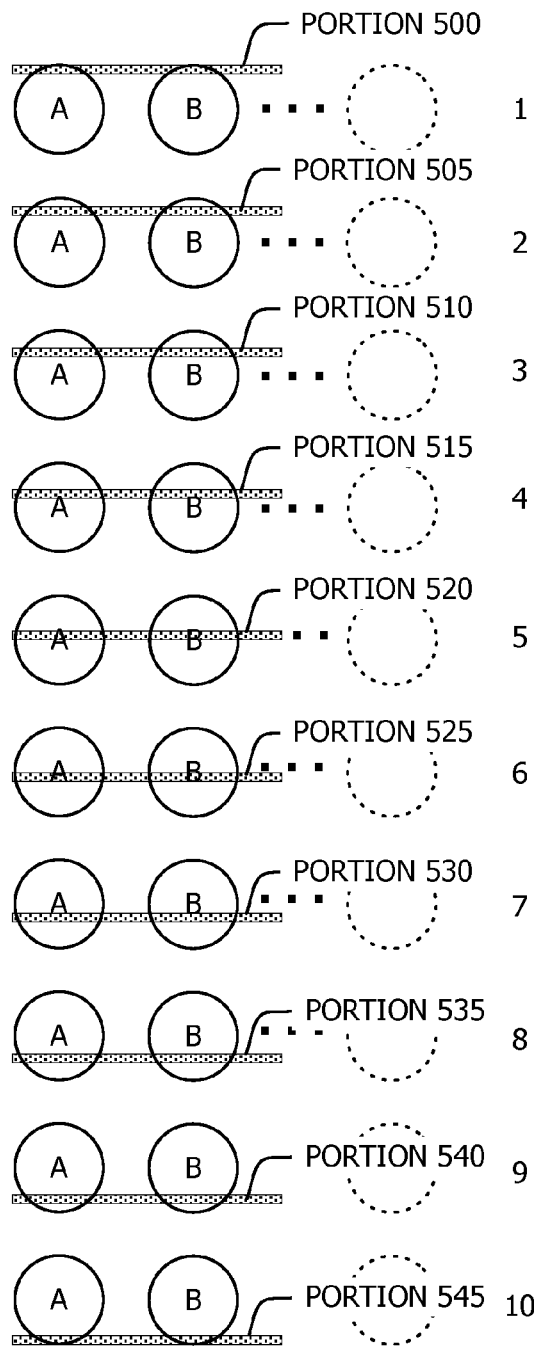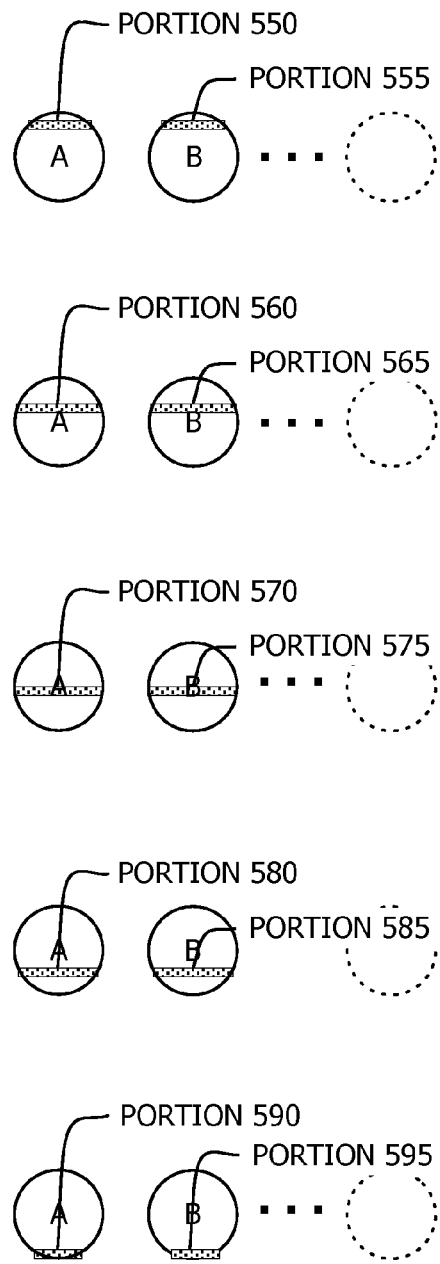
FIG. 5A
FIG. 5B

HIGH THROUGHPUT IMAGING DEVICE AND METHOD

RELATED APPLICATIONS

This application claims priority to U.S. provisional application No. 60/674,520, entitled "High Throughput Wavelength Limited Cellular Analysis Apparatus and Method," filed 25 Apr. 2005 and which is hereby incorporated by reference.

BACKGROUND

The invention relates generally to the field of cellular and subcellular analysis and more particularly, but not by way of limitation, to high throughput imaging devices and systems for use in cellular, sub-cellular and tissue analysis.

Traditional microscopy includes well-known techniques to view and image tissues, cells and subcellular structures. Using one or more light sources (sequentially or in combination) to obtain bright field, dark field, fluorescent, phase contrast or polarization information, image data can be collected by moving a microscope slide, or other cellular container, into the path of a stationary light source and objective. Moving the slide or sample container is typically a slow operation (e.g., 40 micron steps) to accommodate a limited field-of-view ("FOV"). The resolving limit of a light microscope is approximately 0.2 micron (often refereed to as wavelength limited), thus requiring approximately ±0.05 micron of translation resolution in the plane of the viewing field (hereinafter referred to as the horizontal ("x") and vertical ("y") axes). The high-resolution requirements for the component moving the sample container combined with the large area of a typical microscope slide (400 micron$^2$ to 800 micron$^2$), impose sever limits on transnational speeds. In these instruments, x-y translation is further encumbered by the time lost due to deceleration, acceleration, and backlash compensation of the moving component between each step or movement.

One current attempt to increase the analysis throughput of microscopy-based devices involves the analysis of quantities of reagents or analytes in the microliters using what are known as microwell plates or arrays. Existing microwell technology uses 96, 384 and 1,536 microwell plates, wherein each well can retain between approximately 1 microliter and 1 milliliter of liquid. In instruments designed to accommodate microwell plates, a light source is placed beneath a cell and an objective above the cell such that a top-down cellular view is obtained. This approach is stressed in the literature because it tends to reduce any interposed refractive index changes caused by the microwell structure itself. While many standard objectives can compensate for the typical bottom thickness of a microwell (e.g., 170 microns), they exponentially lose resolving power as the thickness increases. For example, a millimeter thick microwell bottom can obscure subcellular detail using standard, uncompensated, objectives. Another recognized drawback to microscopes designed to view and image microwell-based samples is the difficulty of accurately aligning the well structure (most microwells have a curved bottom) to the axis of the objective. For example, to achieve wavelength limited resolution it is typically necessary to use an objective having a high magnification ($\geq 60\times$) and a numerical aperture $\geq 0.7$. This combination in a standard microscope objective can result in a short depth of field—on the order of 0.1 micron to 0.8 micron (the "z" axis). Accordingly, if the microwell bottom is tilted beyond 1 micron in the FOV, important data in the image plane can be out of focus, resulting in the loss of information.

Thus, it would be beneficial to provide a device and system that is capable of high throughput imaging of multiple samples at a high resolution and that overcomes the acknowledged drawbacks to existing imaging systems.

SUMMARY

In one embodiment the invention provides a device to image one or more sample volumes as they are rotated under a detector. The device includes a platform oriented in a plane having secured therein/thereon a plurality of sample volumes, a motor configured to rotate the platform in the plane, one or more light sources on a first side of the platform and a detector configured to move from a first position over a second side of the platform to a second position over the second side of the platform and further configured to collect at least some of the transmitted light, while the platform is rotated, to form an image of at least a portion of one or more of the sample volumes. In some embodiments, the platform is used to secure one or more multi-sample containers (e.g., microwell plates) while in other embodiments the sample volumes could be integral to the platform itself. In still other embodiments, the rate at which the platform is altered as the detector is moved from the first position to the second position to ensure that the area passing under the camera within any given period of time is substantially the same (regardless of its position relative to the second surface of the platform). In yet other embodiments, light sources on the second side of the platform (for epi-illumination operations) rather than, or in combination with, the aforementioned light sources on the first side of the platform may be provided.

In still another embodiment, the invention provides a method to image one or more sample volumes disposed in a platform. The method includes disposing samples in at least some of the one or more sample volumes, continuously rotating the platform, transmitting light from one or more light sources on a first side of the platform and moving a detector from a first position to a second position over a second side of the platform, wherein the detector collects at least some of the transmitted light to form an image of at least a portion of one or more of the one or more sample volumes. Methods in accordance with the invention may also make use of light sources on the second side of the platform for epi-illumination operations.

BRIEF DESCRIPTION OF THE DRAWINGS

FIGS. 5A and 5B show, in schematic form, two image capture approaches in accordance with the invention.

DETAILED DESCRIPTION

Cytometric devices and systems capable of high throughput imaging of multi-sample containers are described. The following description is presented to enable any person skilled in the art to make and use the invention as claimed and is provided in the context of the particular examples discussed below, variations of which will be readily apparent to those skilled in the art. Accordingly, the claims appended hereto are not intended to be limited by the disclosed embodiments, but are to be accorded their widest scope consistent with the principles and features disclosed herein.

Figure 1:
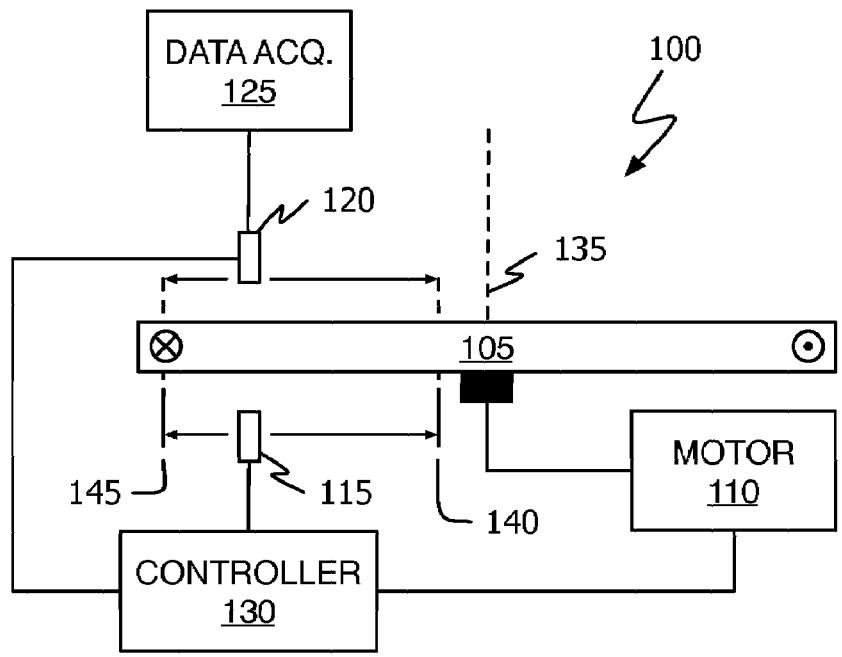
FIG. 1 shows, in block diagram form, a high throughput imaging device in accordance with one embodiment of the invention.

Referring to FIG. 1, high throughput imaging device 100 in accordance with one embodiment of the invention includes rotating platform 105, motor unit 110, light source 115, image capture device 120, data acquisition module 125 and device controller 130. In the illustrated embodiment, platform 105 rotates about axis 135 perpendicular to the plane of FIG. 1. For example, the left edge of platform 105 rotates into the plane of FIG. 1 (denoted by the symbol ⊗) while the right edge of platform 105 rotates out of the plane of FIG. 1 (denoted by the symbol ⊙).

In general, during operation controller 130 causes motor 110 to continuously rotate platform 105 (having one or more multi-sample containers affixed thereon, not shown). Illustrative motors include, but are not limited to, stepper motors and servo motors. While the chosen rotational speed can vary based on a number of factors such as, for example, the type of sample being imaged, the type of illumination used and the duration needed to acquire an image of the desired resolution, the primary function of rotation is not to centrifuge the samples during image acquisition operations but rather to provide a continuous motion so as to increase image acquisition throughput (see discussion below). Concurrent with this rotation, controller 130 also causes light source 115 and imaging device 120 to move radially across platform 105 from a first position (e.g., location 140) to a second position (e.g., location 145)—capturing images of the samples as they pass under image capture device 120. Images are communicated in serial (e.g., via Universal Serial Bus 1.1/2.0 or FireWire/IEEE 1394 ports) or parallel (e.g., via Centronics or Small Computer System Interface ports) to data acquisition module 125 for further processing (see discussion below).

Figure 2:
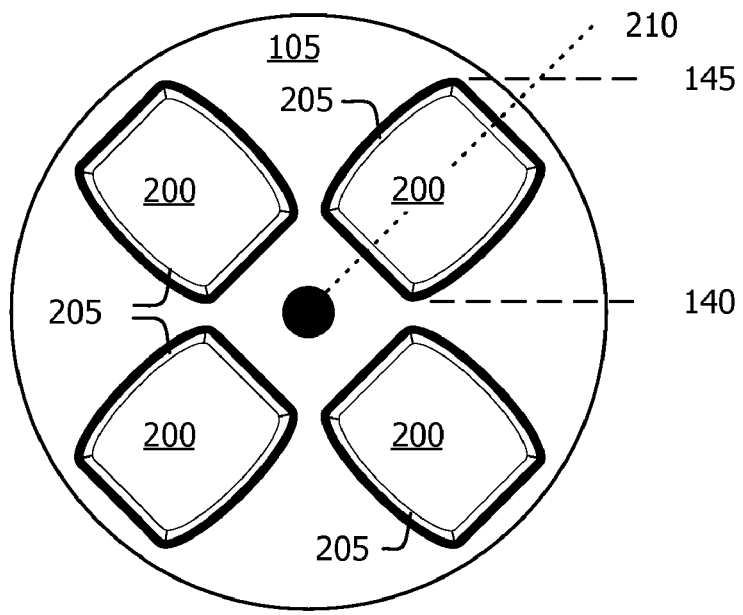
FIG. 2 shows a top-down view of a rotating platform in accordance with FIG. 1.

Referring to FIG. 2, A top-down view of platform 105 is shown for an embodiment which includes slots 200 for securing four multi-sample containers. Illustrative multi-sample containers include, but are not limited to, microwell plates, and microscope slides. As shown, slots 200 have ledges 205 on which multi-sample containers rest—thereby permitting light from light source 115 to pass up through the bottom of the containers and be collected by image capture device 120 and data acquisition module 125 (see FIG. 1). Thus, in the illustrated embodiment, platform 105 is constructed such that multi-sample containers are retained within recesses (e.g., slots 200) within platform 105. One of ordinary skill in the art will recognize that this is not the only approach possible. For example, multi-sample containers could be affixed to a surface of platform 105 or the platform itself could be fabricated having multi-sample wells therein. In this latter embodiment, various numbers of samples could be accommodated by using different platforms. For example, a first platform may include 100 samples while a second platform may include 300 samples.

Also shown in FIG. 2 are locations 140, 145 (see FIG. 1) and radial movement mark 210. As well be discussed in more detail below, during operation platform 105 is continuously rotated while light source 115 and image capture device 120 are periodically moved along movement mark 210 (radially) between a starting position (e.g., 140) and an ending position (e.g., 145).

Figure 3:
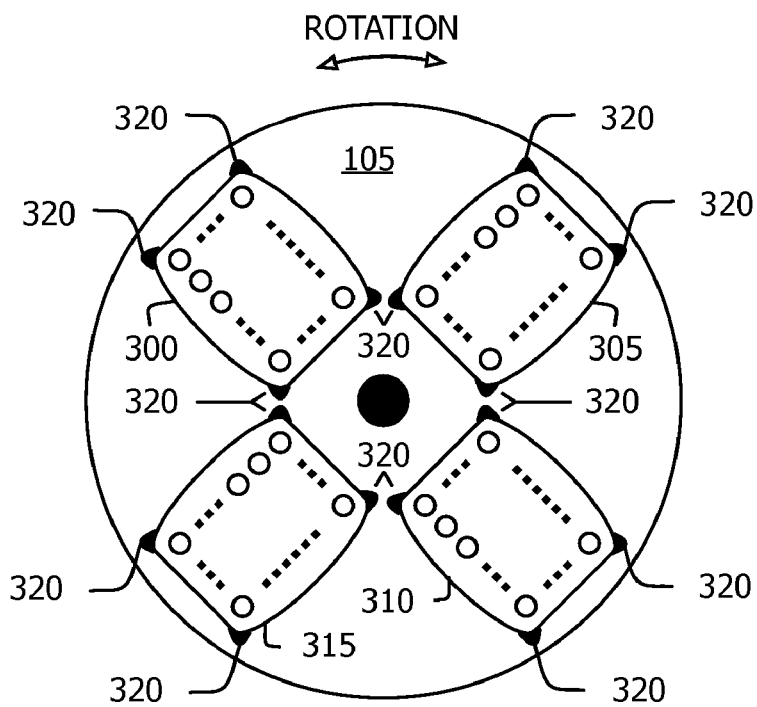
FIG. 3 shows a top-down view of a rotating platform having four multi-sample containers affixed thereto.

Referring to FIG. 3, platform 105 of FIG. 2 is shown with four multi-sample containers affixed thereto. In this embodiment, multi-sample containers 300, 305, 310 and 315 are kept in place by spring-loaded edge connectors 320. Connectors 320 and slots 200 retain multi-sample containers 300, 305, 310 and 315 so they do not shift or move during image capture operations.

Figure 4:
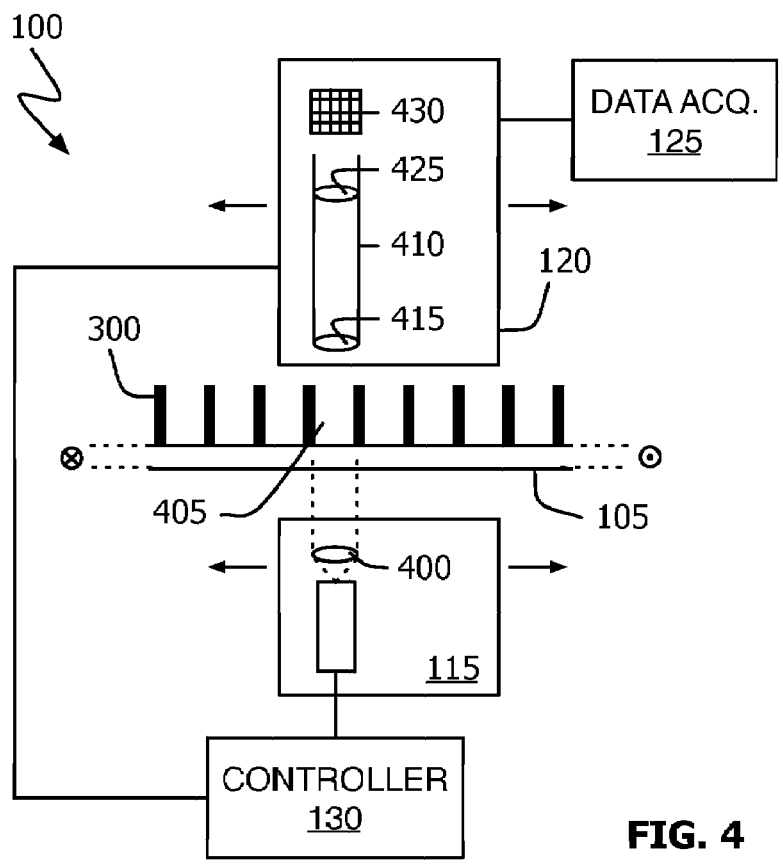
FIG. 4 shows, in block diagram form, an expanded view of an image device in accordance with FIG. 1.

Referring now to FIG. 4, during operation controller 130 causes platform 105 to rotate and light source 115 and image capture device 120 to move radially across a multi-sample container (see FIGS. 1-3). As platform 105 is rotated, light from light source 115 passes through one or more lens 400 configured to provide uniform illumination of samples disposed in, for example, volume 405 of multi-sample container 300. In one embodiment, light source 115 comprises an array of white light emitting diodes ("LEDs") arranged or configured into an approximate circle. In another embodiment, the LEDs are also arranged into a circle structure but individually powered—power to the peripheral LEDs being greater than power to the central LEDs to yield a rapid increase in illumination at the periphery with spatially uniform illumination in the center. In yet another embodiment, light source 115 comprises multiple illumination sources—one white light source (e.g., for bright and dark field measurements) and one or more colored light sources (e.g., for fluorescence measurements). Illustrative colored light sources include those in the range of approximately 300 nanometers ("ultraviolet") to approximately 800 nanometers ("infrared"). Physical light sources include, but are not limited to, arc lamps, continuous wave lasers, modulated lasers, pulsed-lasers, laser diodes and LEDs. In general, preferred embodiments of light source 115 include various wavelength LEDs aligned to a common optical path through one or more matched dichroic filters or reflectors (e.g., lens 400) to provide circular illumination. Other common optic elements that may be used to provide uniform illumination of the light source include one or more of the following: collimating lens, beam expanders, condenser lens and focusing lens.

As the light from light source 115 passes through volume 405 (directly or via scattering) or is emitted (e.g., in the case of fluorescence or chemiluminescence) from a sample in volume 405, it is captured by device 120. In the illustrated embodiment, device 120 comprises an optical bench unit 410 housing optical elements 415 and 425 and detector 430. Generally speaking, element 415 is an objective lens while component 425 may be zero or more additional components such as, for example, filter(s), relay lens and secondary focus lens. Optical element 425 generally comprises a filter to block light above a certain wavelength from entering detector 430. Detector 430 can use any device that is capable of line-capture operations. Example detectors include, but are not limited to, photomultiplier tubes ("PMTs"), photo-diodes and various versions of complementary metal-oxide semiconductor ("CMOS") and charge couple device ("3D") camera devices configured for line scan operations. In one embodiment, detector 430 comprises a timed delayed integration ("TDI") 3D camera. As previously noted, as images are captured by detector 430, they are communicated to image acquisition module 125 where they are processed (e.g., color corrected and assembled into complete images).

It will be recognized that as platform 105 is rotated and as the light source 115 (and associated lenses) and image capture device 120 are moved as described, various sample volumes will be interrogated. With current technology detectors (e.g., detector 430), it is generally not possible to image an entire sample volume (e.g., volume 405) at once with the resolution needed for cellular and sub-cellular analysis. Accordingly, images for each volume are obtained one portion at a time—the collection of such images for a given sample volume being stitched together by data acquisition module 125.

Referring to FIG. 5A, in one embodiment sample volume images are obtained one "row" at a time. That is, during a first revolution of platform 105 an image of a first portion of the sample volumes (e.g., volumes A and B) rotated under image device 120 is captured (e.g., portion 500). (In FIGS. 5A and 5B, each rotation of platform 105 is denoted by a numeric value 1 through 10.) After a first revolution of platform 105, light source 115 and image device 120 are moved radially along platform 105 to capture a second portion 505 of the sample volumes. This process is repeated until all of the desired sample volumes have been imaged (e.g., images portions 500-545). As noted above, each of images 500-545 are communicated to data acquisition module 125 which "stitches" the portions together to provide complete images of each sample volume.

Referring to FIG. 5B, in another embodiment image capture operations are limited to those regions known to include sample volumes. In this approach, partial images of each sample volume (e.g., 550-595) are captured during each revolution of platform 105. It will be recognized that image capture in accordance with FIG. 5B requires an a priori knowledge of where each sample volume is (relative to some known or fixed location) so that image capture operations can be stopped and started at the appropriate times. Because the size of each multi-sample container, the number of samples in each multi-sample container, the physical layout of sample volumes within each multi-sample container, the location of each multi-sample container on platform 105 and the location of image capture device 120 are known, this information is easily determined.

While FIGS. 5A and 5B show sample volumes (e.g., volumes A and B) are completely imaged in 10 steps, one of ordinary skill in the art will recognize that it can take many more that ten steps to capture all of a sample volume. In one embodiment, for example, detector 430 comprises a TDI camera that captures 10 lines at a time, with each line being approximately 0.1 micron in width and 10 microns in length. Accordingly, in this embodiment the number of image portions needed to completely capture each sample volume on, for example, a microwell plate having 384 sample volumes, can be many thousands.

Figure 6:
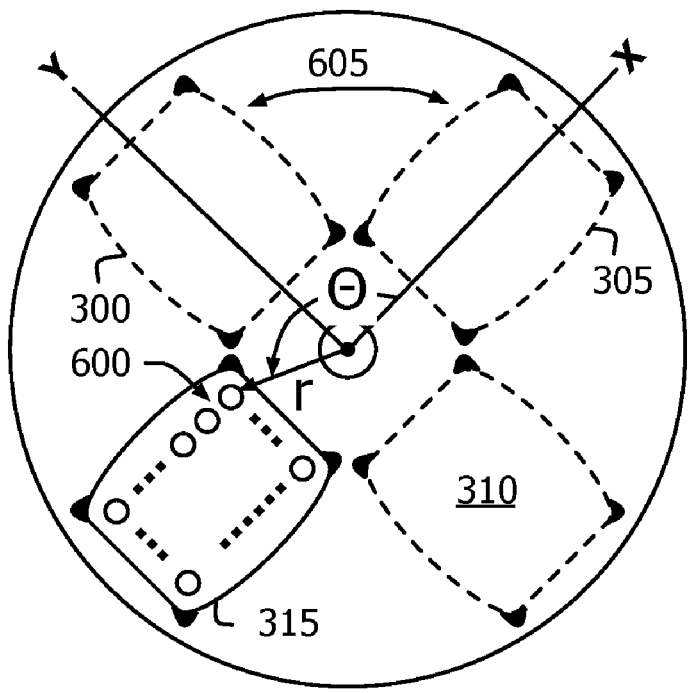
FIG. 6 shows a reference system in accordance with one embodiment of the invention.

Referring to FIG. 6, in one embodiment a "zero" location is positioned at the center of platform 105—coincident with the platform's axis of rotation 135. From this a coordinate system may be defined (denoted with "x" and "y" axes). Within this arbitrary but fixed coordinate system, the location of each sample volume may be uniquely defined by pairs of angle ($\Theta$) and radial distance (r). It will be appreciated that each sample volume may be associated with a plurality of ($\Theta$, r) pairs so that the perimeter of each sample volume can be uniquely determined. It will also be appreciated that this knowledge permits image capture device 120 to not capture data when it is positioned over regions not containing samples. For example, when image capture device 120 is over a region between sample volumes (e.g., 600) or between multi-sample containers (e.g., 605). One benefit of this approach is that the amount of image data that must be processed can be substantially reduced over that captured in accordance with the approach illustrated in FIG. 5A.

Figure 7:
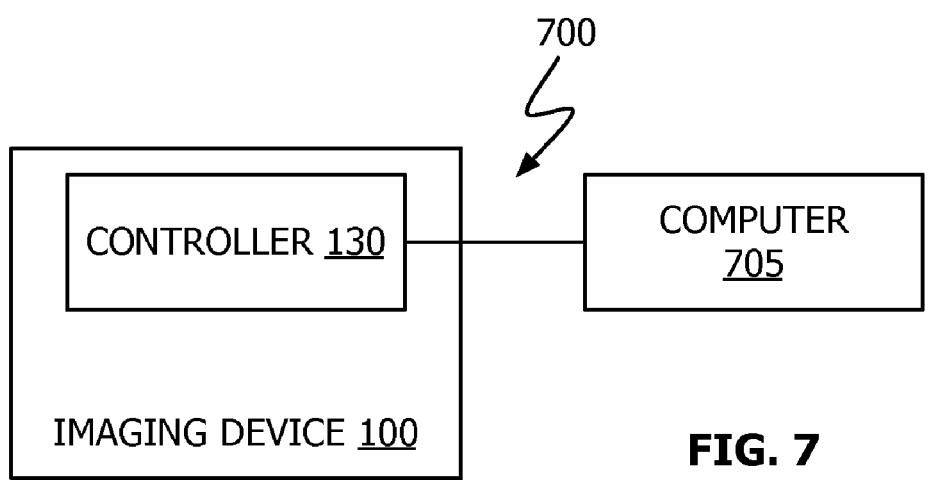
FIG. 7 shows, in block diagram form, an imaging system in accordance with one embodiment of the invention.

In one embodiment, controller 130 incorporates the information needed to start and stop detector 430 from capturing data for any one of a predetermined number of types of multi-sample containers. Referring to FIG. 7, in another embodiment imaging system 700 comprises imaging device 100 communicatively coupled to computer system 705. In this embodiment, computer system 705 permits a user to identify which one of a predetermined number of multi-sample containers are affixed to platform 105, where after this information (including when to start and stop image capture operations) is downloaded to controller 130. In this latter embodiment, it may be beneficial to store the information downloaded from computer system 700 to controller 430 in field programmable gate arrays ("FPGAs". Illustrative computer systems include, but are not limited to, computers systems running the Windows,® Mac OS,® Unix® or Linux operating systems. (WINDOWS is a registered trademark of the Microsoft Corporation of Redmond, Wash. MAC OS is a registered trademark of Apple Computer, Inc. of Cupertino, Calif. UNIX is a registered trademark of Unix System Laboratories, Inc. of Basking Ridge, N.J.)

Figure 8:
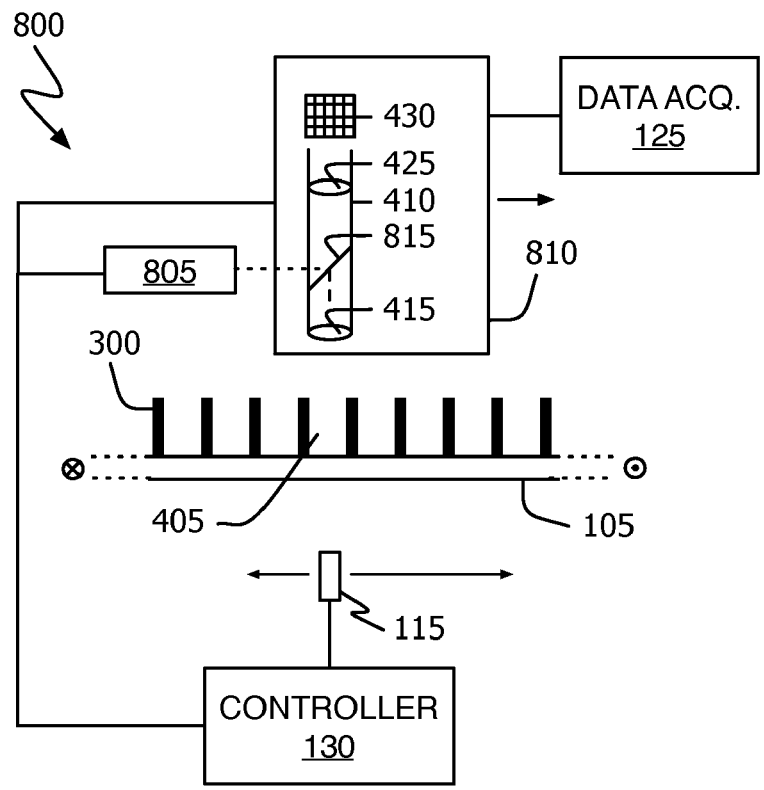
FIG. 8 shows, in block diagram form, a high throughput imaging device in accordance with another embodiment of the invention.
Figure 9:
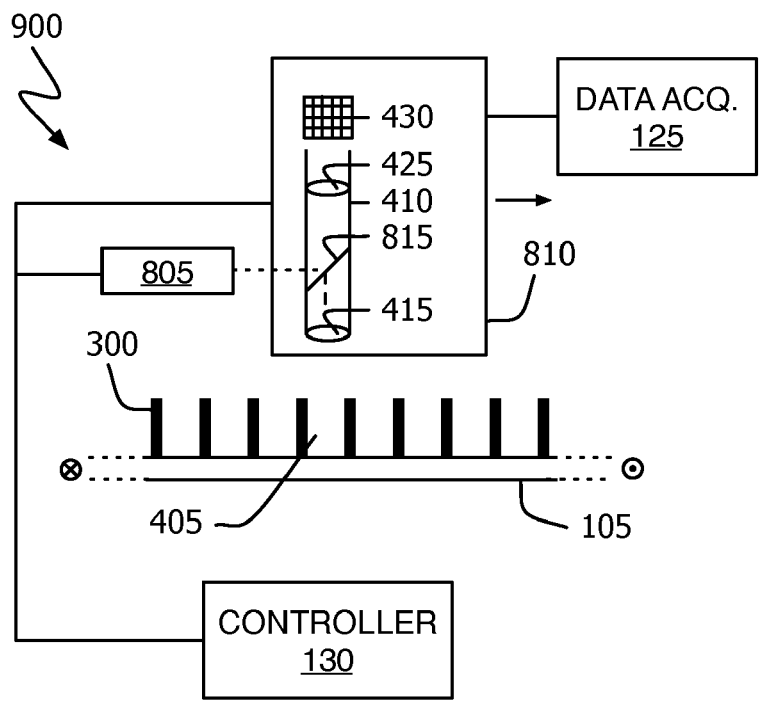
FIG. 9 shows, in block diagram form, a high throughput imaging device in accordance with another embodiment of the invention.

Referring to FIG. 8, imaging device 800 in accordance with another embodiment of the invention includes light source 115 for illuminating sample volumes from a first side and one or more light sources 805 for illuminating sample volumes from a second side (e.g., volume 405). Device 800 is particularly useful for fluorescence operations which, typically, use epi-illumination. In this embodiment, light source 805 can be any source of light suitable for fluorescing the desired sample. During operation, light emitted by light source 115 passes through (directly and/or via scattering) the target sample volume (e.g., volume 405) and into image capture device 810 where it passes through optical component 415 (e.g., an objective lens) reflector 815 and element 425 before being captured by detector 430. Light from light source 805 is reflected by reflector 810 (e.g., a dichroic mirror, polarizing mirror or refractive mirror) down onto platform 105 and, in particular, the sample volume positioned under image capture device 810. Light emitted by constituents in the sample as a result of light from source 805 is captured in the same manner as light originally emitted from source 115. It will be recognized that light source 805 is moved by controller 130 in unison with image capture device 810 and light source 115. It will further be recognized that light source 805 may comprise more than one light source. For example, a separate light source may be used for each of a specified number of wavelengths. Referring to FIG. 9, in yet another embodiment of the invention, light source 115 may be omitted. In this case, imaging device 900 provides epi-illumination only.

It will be recognized that one benefit of the architecture outlined here (see FIGS. 1-9) is that sample volumes are imaged during each revolution of platform 105 without the need to compensate for any motion artifacts (e.g., acceleration, deceleration or backlash) associated with periodically moving the sample volumes. Further, it has been found that if the light source 115 and imaging device 120 (the "imaging system") are moved after each rotation during the time that it (the imaging system) is between multi-sample containers—e.g., in region 605—no imaging time is lost due to image system motion artifacts. Accordingly, an imaging system in accordance with the invention permits near continuous imaging of multiple samples to provide a high throughput imaging device for cellular, sub-cellular and tissue analysis purposes.

In one embodiment, while platform 105 is continuously rotated during image capture operations, its rotational velocity or speed is adjusted depending upon where image capture device 120 or 810 is positioned. For example, platform 105 may be rotated at a speed of 10,000 microns/second when image capture device 120/810 is positioned over a peripheral region of the platform (e.g., location 145) and gradually slowed to 1,000 microns/second as it is brought closer to the center of platform 105 (e.g., location 140). This change in rotational speed is to compensate for the area that imaging device 120/810 "sees" as it is moved radially across rotating platform 105. The precise starting rotational speed, ending rotational speed and the change in speed when moving from the peripheral to central locations on platform 105 is largely dependent upon the precise type of detector 430 used. One of ordinary skill in the art will recognize that the rotational speed must be slow enough that detector 430 can capture an image without introducing motion artifacts.

Various changes in the materials and components are possible without departing from the scope of the following claims. For instance, platform 105 need not be circular. In addition, platform 105 could house fewer or more than the demonstrated four multi-sample containers. Further, platform 105 could itself be a multi-sample container. By way of example, a first platform may include 100 integral sample volumes while a second platform may include 300 integral sample volumes.

It will also be recognized by those of ordinary skill in the art that platform 105 could be centrifuged before or after image capture operations as described herein. It will further be recognized that, while a single image capture device has been described (e.g., devices 120 and 810), it is possible to include more than one such device in a system in accordance with the claimed invention. It will also be recognized that image processing could be performed away from imaging device 100 or 800. That is, raw image data from detector 430 could be communicated to a computer system (e.g., computer system 705) where it is processed (e.g., stitched together) and displayed.

The invention claimed is:

1. A rotating imaging device, comprising:
   a platform oriented in a plane and configured to secure one or more multi-sample container units;
   a motor configured to rotate the platform in the plane;
   one or more light sources on a first side of the platform configured to transmit light from the first side of the platform toward a second side of the platform;
   one or more light sources on the second side of the platform configured to transmit light from the second side of the platform toward the first side of the platform; and
   a detector configured to move from a first position over the second side of the platform to a second position over the second side of the platform and further configured to collect at least some of the transmitted light from the light sources on the first side of the platform and at least some of the transmitted light from light sources on the second side of the platform, while the platform is rotated, to form an image of at least a portion of one or more samples disposed in the one or more multi-sample container units.

2. The rotating imaging device of claim 1, wherein the platform comprises a circular disc configured to rotate in the plane of the disk.

3. The rotating imaging device of claim 1, wherein the multi-sample container units comprise microwell plates.

4. The rotating imaging device of claim 1, wherein the multi-sample container units comprise microscope slides.

5. The rotating imaging device of claim 1, wherein the motor is configured to continuously rotate the platform in the plane of the platform during imaging operations.

6. The rotating imaging device of claim 5, wherein the motor is configured to slow the rate at which the platform is rotated as the detector is moved from the first position to the second position.

7. The rotating imaging device of claim 1, wherein the detector is configured to move from the first position to the second position in a series of steps, each step occurring during a time when the detector is above a portion of the platform that does not contain a multi-sample container unit.

8. The rotating imaging device of claim 1, wherein the detector is configured to move from the first position to the second position in a series of steps, each step occurring during a time when the detector is not above a sample disposed in the one or more multi-sample container units.

9. The rotating imaging device of claim 1, wherein the one or more light sources comprise a white light source.

10. The rotating imaging device of claim 1, wherein the one or more light sources on the first side comprise one or more sources of light between approximately 30 nanometer and approximately 800 nanometers.

11. The rotating imaging device of claim 1, wherein at least one of the one or more light sources on the first side comprise a light emitting diode.

12. The rotating imaging device of claim 1, wherein at least one of the one or more light sources on the first side comprise a laser.

13. The rotating imaging device of claim 1, wherein the detector comprises a charge coupled device.

14. The rotating imaging device of claim 13, wherein the charge coupled device comprised a time delay integration camera.

15. The rotating imaging device of claim 1, wherein at least one of the one or more light sources on the second side of the platform emit light in the range of approximately 30 nanometers to 800 nanometers.

16. The rotating imaging device of claim 1, wherein at least one of the one or more light sources on the second side of the platform comprise a laser.

17. The method of claim 1, further comprising:
   transmitting light from one or more light sources on the second side of the platform onto a sample; and
   collecting, by the detector, light emitted from the sample as a result of the light transmitted by the one or more light sources on the second side of the platform.

18. The method of claim 17, wherein the act of transmitting light from one or more light sources on the second side of the platform comprises transmitting light in the range of approximately 30 nanometers to 800 nanometers.

19. An imaging device, comprising:
   a platform oriented in a plane having a plurality of sample volumes disposed therein;
   a motor configured to rotate the platform in the plane;
   one or more light sources on a first side of the platform configured to transmit light;

one or more light sources on a second side of the platform configured to transmit light; and a detector configured to move from a first position over the second side of the platform to a second position over the second side of the platform and further configured to collect at least some light transmitted from the light sources on the first side of the platform and at least some light transmitted from the light sources on the second side of the platform, while the platform is rotated, to form an image of at least a portion of one or more of the sample volumes.

20. The imaging device of claim 19, wherein the platform comprises a circular disc configured to rotate in the plane of the disk.

21. The imaging device of claim 19, wherein the motor is configured to continuously rotate the platform in the plane of the platform during imaging operations.

22. The imaging device of claim 21, wherein the motor is configured to slow the rate at which the platform is rotated as the detector is moved from the first position to the second position.

23. The imaging device of claim 19, wherein the detector is configured to move from the first position to the second position in a series of steps, each step occurring during a time when the detector is above a portion of the platform that does not contain a sample volume.

24. The imaging device of claim 19, wherein the one or more light sources comprise a white light source.

25. The imaging device of claim 19, wherein the one or more light sources on the first side comprise one or more sources of light between approximately 30 nanometer and approximately 800 nanometers.

26. The imaging device of claim 19, wherein at least one of the one or more light sources on the first side comprise a light emitting diode.

27. The imaging device of claim 19, wherein at least one of the one or more light sources on the first side comprise a laser.

28. The imaging device of claim 19, wherein the detector comprises a charge coupled device.

29. The imaging device of claim 28, wherein the charge coupled device comprised a time delay integration camera.

30. The imaging device of claim 19, wherein at least one of the one or more light sources on the second side of the platform emit light in the range of approximately 30 nanometers to 800 nanometers.

31. The rotating imaging device of claim 19, wherein at least one of the one or more light sources on the second side of the platform comprise a laser.

32. A rotating imaging device, comprising:
a platform oriented in a plane and configured to secure one or more multi-sample container units;
a motor configured to rotate the platform in the plane;
a detector configured to move from a first location over a first side of the platform to a second location over the first side of the platform;
one or more light sources on the first side of the platform configured to transmit light toward the platform along an optical axis of the detector; and
one or more light sources on the second side of the platform configured to transmit light toward the platform,
wherein the detector is configured to collect, while the platform is rotated (i) at least some light emitted from a sample disposed in the one or more multi-sample containers as a result of the light transmitted by the one or more light sources on the first side of the platform and (ii) at least some of the light transmitted by the one or more light sources on the second side of the platform.

33. A rotating imaging device, comprising:
a platform oriented in a plane having a plurality of sample volumes disposed therein;
a motor configured to rotate the platform in the plane;
a detector configured to move from a first location over a first side of the platform to a second location over the first side of the platform;
one or more light sources on the first side of the platform configured to transmit light toward the platform along an optical axis of the detector; and
one or more light sources on the second side of the platform configured to transmit light toward the platform,
wherein the detector is configured to collect, while the platform is rotated (i) at least some light emitted from a sample disposed in the sample volumes as a result of the light transmitted by the one or more light sources on the first side of the platform and (ii) at least some of the light transmitted by the one or more light sources on the second side of the platform.

* * * * *